United States Patent
Kiyomiya et al.

(10) Patent No.: US 10,842,875 B2
(45) Date of Patent: Nov. 24, 2020

(54) OPHTHALMIC COMPOSITION

(71) Applicant: ROHTO PHARMACEUTICAL CO., LTD., Osaka (JP)

(72) Inventors: Aki Kiyomiya, Osaka (JP); Takahiro Kurose, Osaka (JP); Atsuko Nakata, Osaka (JP); Xiang Zheng, Osaka (JP)

(73) Assignee: ROHTO PHARMACEUTICAL CO., LTD., Osaka (JP)

(*) Notice: Subject to any disclaimer, the term of this patent is extended or adjusted under 35 U.S.C. 154(b) by 70 days.

(21) Appl. No.: 15/766,514

(22) PCT Filed: Nov. 22, 2016

(86) PCT No.: PCT/JP2016/084522
§ 371 (c)(1),
(2) Date: Apr. 6, 2018

(87) PCT Pub. No.: WO2017/094552
PCT Pub. Date: Jun. 8, 2017

(65) Prior Publication Data
US 2018/0289812 A1  Oct. 11, 2018

(30) Foreign Application Priority Data
Nov. 30, 2015 (JP) ................. 2015-232910

(51) Int. Cl.
| | |
|---|---|
| *A61K 47/32* | (2006.01) |
| *A61K 47/26* | (2006.01) |
| *A61K 47/44* | (2017.01) |
| *A61K 9/00* | (2006.01) |
| *A61P 27/02* | (2006.01) |
| *A61K 47/34* | (2017.01) |
| *G02C 7/04* | (2006.01) |
| *A61K 47/10* | (2017.01) |
| *A61K 47/38* | (2006.01) |
| *A61K 47/18* | (2017.01) |
| *A61K 47/36* | (2006.01) |
| *A61K 47/02* | (2006.01) |

(52) U.S. Cl.
CPC ............ *A61K 47/32* (2013.01); *A61K 9/0048* (2013.01); *A61K 47/02* (2013.01); *A61K 47/10* (2013.01); *A61K 47/186* (2013.01); *A61K 47/26* (2013.01); *A61K 47/34* (2013.01); *A61K 47/36* (2013.01); *A61K 47/38* (2013.01); *A61K 47/44* (2013.01); *G02C 7/04* (2013.01)

(58) Field of Classification Search
CPC ...... A61K 47/32; A61K 47/44; A61K 9/0048; A61P 27/02
See application file for complete search history.

(56) References Cited

U.S. PATENT DOCUMENTS

| | | | |
|---|---|---|---|
| 2007/0265353 A1* | 11/2007 | Matsuhisa | ............ A61K 9/0048 514/762 |
| 2009/0057164 A1 | 3/2009 | Minick et al. | |
| 2010/0239518 A1* | 9/2010 | Matsumura | ............ A61P 27/04 424/78.04 |

FOREIGN PATENT DOCUMENTS

| | | | |
|---|---|---|---|
| CN | 101854939 A | | 10/2010 |
| JP | 1-294620 A | | 11/1989 |
| JP | 2005-206598 A | | 8/2005 |
| JP | 2010-538321 A | | 12/2010 |
| JP | 2011-8072 A | | 1/2011 |
| JP | 2012031075 A | * | 2/2012 |
| JP | 2014-15453 A | | 1/2014 |
| JP | 2014015453 A | * | 1/2014 |
| WO | 2009/032122 A1 | | 3/2009 |
| WO | 2009/035034 A1 | | 3/2009 |
| WO | 2016/190306 A1 | | 12/2016 |

OTHER PUBLICATIONS

La Rosa, M., Lionetti, E., Reibaldi, M. et al. "Allergic conjunctivitis: a comprehensive review of the literature." Ital J Pediatr (2013) 39:18. https://doi.org/10.1186/1824-7288-39-18.*
Notification of Transmittal of Translation of the International Preliminary Report on Patentability (Form PCT/IB/338) issued in counterpart International Application No. PCT/JP2016/084522 dated Jun. 14, 2018, with Forms PCT/IB/373 and PCT/ISA/237. (11 pages).
International Search Report dated Dec. 27, 2016, issued in Counterpart of International Application No. PCT/JP2016/084522 (2 pages).

* cited by examiner

Primary Examiner — Bethany P Barham
Assistant Examiner — Peter Anthopolos
(74) Attorney, Agent, or Firm — Westerman, Hattori, Daniels & Adrian, LLP

(57) ABSTRACT

The inventive ophthalmic composition comprises: (A) polyvinyl pyrrolidone K90; and (B) at least one selected from the group consisting of an oil component, a grease component and polyethylene glycol. The ophthalmic composition alleviates a sticky sensation to ensure an excellent use sensation.

9 Claims, 1 Drawing Sheet

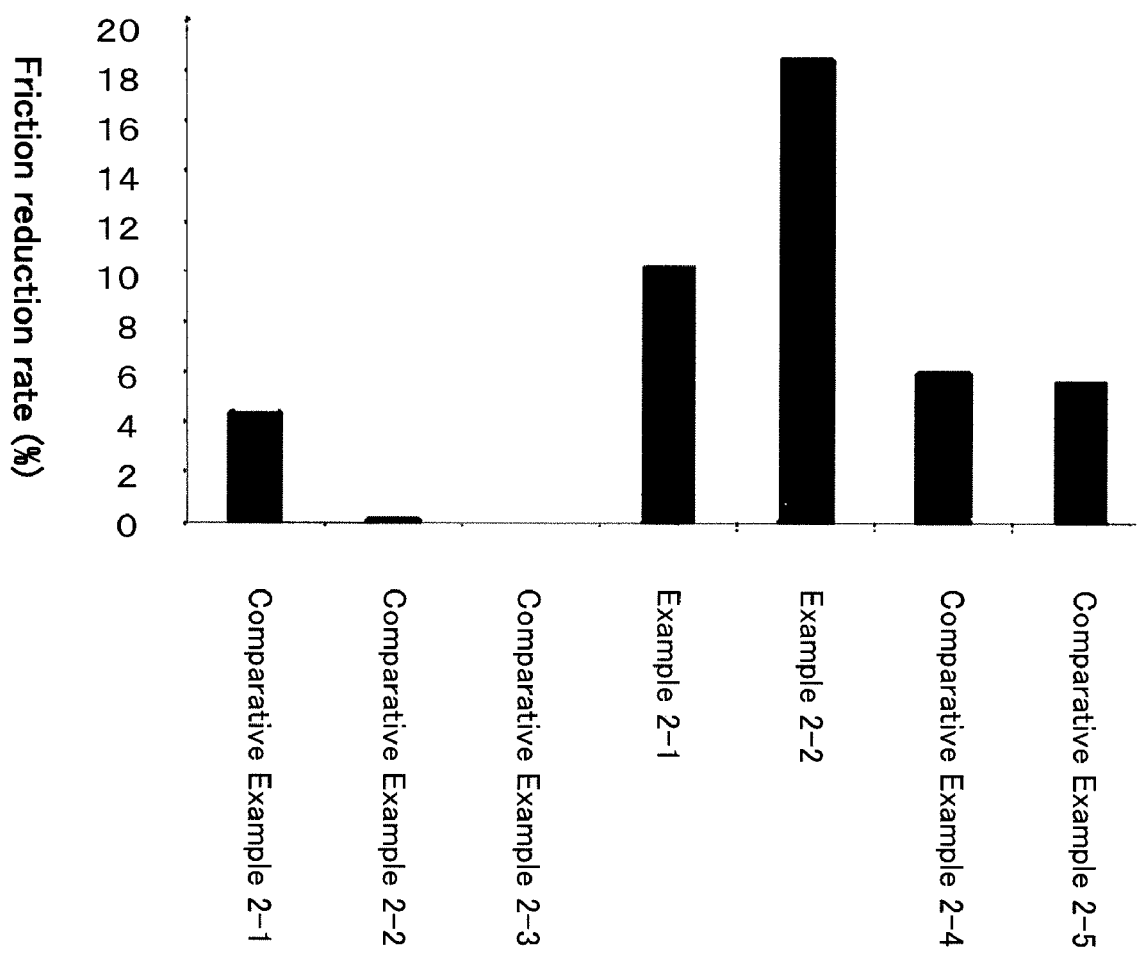

OPHTHALMIC COMPOSITION

TECHNICAL FIELD

The present disclosure relates to an ophthalmic composition.

BACKGROUND ART

In the field of ophthalmic compositions, polyvinyl pyrrolidone is used, for example, as a solubilizing agent or the like (PTL 1).

On the other hand, polyethylene glycol is known as an isotonizing agent or the like in the field of ophthalmic compositions. Currently, studies are not sufficiently conducted on how addition of polyethylene glycol to a polyvinyl pyrrolidone-containing ophthalmic composition influences the use sensation of the ophthalmic composition.

RELATED ART DOCUMENT

Patent Document

PTL 1: JP-A-HEI1(1989)-294620

SUMMARY OF INVENTION

It is an object of the present disclosure to provide an ophthalmic composition which ensures an excellent use sensation.

The inventors conducted intensive studies to achieve the aforementioned object. As a result, the inventors found that, where polyvinyl pyrrolidone K90 is used as a component for an ophthalmic composition, the ophthalmic composition suffers from an additional problem such that a sticky sensation occurs on eye surfaces and eyelids. The inventors further found that, where the ophthalmic composition contains: (A) polyvinyl pyrrolidone K90; and (B) at least one selected from the group consisting of an oil component, a grease component and polyethylene glycol, the ophthalmic composition is unexpectedly liquid with the sticky sensation alleviated. Thus, the inventors attained the present disclosure.

More specifically, the present disclosure has the following features [1] to [7]:

[1] An ophthalmic composition is provided, which comprises: (A) polyvinyl pyrrolidone K90; and (B) at least one selected from the group consisting of an oil component, a grease component and polyethylene glycol.
[2] In the ophthalmic composition of the feature [1], the oil component of Component (B) is vegetable oil.
[3] In the ophthalmic composition of the feature [1] or [2], the polyethylene glycol of Component (B) has a weight average molecular weight of 100 to 100000.
[4] In the ophthalmic composition of any one of the features [1] to [3], the polyvinyl pyrrolidone K90 of Component (A) is present in a proportion of 0.001 to 10 w/v % based on the total amount of the ophthalmic composition.
[5] The ophthalmic composition of any one of the features [1] to [4] is adapted for a contact lens.
[6] The ophthalmic composition of the feature [5] is adapted for a soft contact lens as the contact lens.
[7] A method for imparting an ophthalmic composition with a friction reducing effect, comprising the step of adding polyvinyl pyrrolidone K90 (Component (A)) and at least one (Component (B)) selected from the group consisting of an oil component, a grease component and polyethylene glycol to the ophthalmic composition.

According to the present disclosure, the ophthalmic composition comprises the polyvinyl pyrrolidone K90 (Component (A)), and at least one (Component (B)) selected from the group consisting of the oil component, the grease component and the polyethylene glycol. Therefore, the ophthalmic composition provides a sticky sensation alleviating effect and a use sensation improving effect when being applied to eyes. Further, the ophthalmic composition is smooth with a reduced frictional resistance with respect to an object (conjunctiva, cornea, a contact lens or the like) to be brought into contact with the ophthalmic composition, and alleviates an uncomfortable sensation and a foreign body sensation, thereby ensuring an excellent use sensation.

BRIEF DESCRIPTION OF DRAWING

FIG. 1 is a graph showing the frictional resistance reduction rates of ophthalmic compositions of inventive examples and comparative examples.

DESCRIPTION OF EMBODIMENTS

Next, embodiments of the present disclosure will be described in detail. However, it should be understood that the disclosure be not limited to these embodiments.

In the present disclosure, the unit "w/v %" for content proportions means weight per volume percentage, and is equivalent to "g/100 mL."

In the present disclosure, the abbreviation "POE" means polyoxyethylene, unless otherwise specified.

In the present disclosure, the abbreviation "POP" means polyoxypropylene, unless otherwise specified.

[1. Ophthalmic Composition]

The inventive ophthalmic composition contains: (A) polyvinyl pyrrolidone K90; and (B) at least one selected from the group consisting of an oil component, a grease component and polyethylene glycol.

The polyvinyl pyrrolidone K90 (Component (A)) is a nonionic water-soluble polymer. The term "K90" means that a viscosity characteristic value (K value) falls within a range of 81.0 to 97.2 as calculated from the following expression (1) based on a relative viscosity measured at 25° C. by means of a capillary viscometer:

$$K = (1.5 \log \eta_{rel} - 1)/(0.15 + 0.003c) + [300c \log \eta_{rel} + (c + 1.5c \log \eta_{rel})^2]^{1/2}/(0.15c + 0.003c^2) \quad (1)$$

wherein $\eta_{rel}$ is the relative viscosity of a polyvinyl pyrrolidone aqueous solution with respect to water, and c is the concentration (%) of polyvinyl pyrrolidone in the polyvinyl pyrrolidone aqueous solution.

The polyvinyl pyrrolidone K90 may be synthesized by a known method, but commercially available products such as AIFUTACT K-90 (available from DKS Co., Ltd.), KORIDON K90 (available from BASF Japan Co., Ltd.), PLASDONE K90 (available from ISP Japan Co., Ltd.) and POVIDONE K90 (available from DSP Gokyo Food & Chemical Co., Ltd.) are usable as the polyvinyl pyrrolidone K90. These commercially available products may be used alone or in combination.

The proportion of Component (A) to be contained is not particularly limited. For example, the total proportion of Component (A) is preferably 0.001 to 10 w/v %, more preferably 0.005 to 5.0 w/v %, further preferably 0.01 to 3.0 w/v %, particularly preferably 0.03 to 1.0 w/v %, based on the total amount of the inventive ophthalmic composition.

These ranges of the proportion of Component (A) are preferred for more remarkably ensuring the effects of the present disclosure. In some case, the total proportion of Component (A) is preferably 0.001 to 0.5 w/v %, particularly preferably 0.005 to 0.1 w/v %.

In the present disclosure, Component (B) to be used in combination with Component (A) is at least one selected from the group consisting of the oil component, the grease component and the polyethylene glycol.

The oil component and the grease component are generally hydrophobic components which are liquid, semisolid or solid at an ordinary temperature (15° C. to 25'C) and are generally usable for pharmaceutical products and quasi-pharmaceutical products. Examples of the oil component and the grease component include vegetable oils such as olive oil, sesame oil, corn oil, camellia oil, soybean oil, rapeseed oil, peanut oil and castor oil, animal oils such as lanolin and squalane, and mineral oils such as liquid paraffin, petrolatum, white petrolatum and ceresin, among which the vegetable oils are preferred for further improvement of the effects of the present disclosure. Further, the sesame oil and the castor oil are more preferred, and the sesame oil is particularly preferred.

The polyethylene glycol is not particularly limited. In general, the polyethylene glycol preferably has a weight average molecular weight of 100 to 100000. In particular, the weight average molecular weight of the polyethylene glycol is preferably 200 to 40000, more preferably 300 to 20000, further preferably 300 to 6000, particularly preferably 400 to 4000, especially preferably 400 to 1000, most preferably 400.

The polyethylene glycol may be synthesized by a known method, but commercially available products such as MACROGOAL 200, 300, 400, 600, 1000, 1500, 1540, 4000, 6000, 20000 and 35000 (available from Adeka Corporation, Sanyo Chemical Industries, Ltd., DKS Co, Ltd., NOF Corporation and the like) are usable as the polyethylene glycol. These commercially available products may be used alone or in combination. Particularly, MACROGOAL 400, 4000 and 6000 are preferred, and MACROGOAL 400 is more preferred.

The oil component, the grease component and the polyethylene glycols described above may be used alone or in combination as Component (B). Of these components as Component (B), the oil component or the grease component is preferred for more remarkably ensuring the effects of the present disclosure.

The proportion of Component (B) to be contained is not particularly limited, but depends on the type of Component (B). The total proportion of Component (B) is preferably 0.00001 to 10 w/v %, more preferably 0.00005 to 5 w/v %, further preferably 0.0001 to 3 w/v %, furthermore preferably 0.0005 to 1 w/v %, based on the total amount of the inventive ophthalmic composition.

Where Component (B) is the oil component or the grease component, the total proportion of the oil component or the grease component is preferably 0.00001 to 10 w/v %, more preferably 0.00005 to 1 w/v %, further preferably 0.0001 to 0.5 w/v %, furthermore preferably 0.0005 to 0.25 w/v %, particularly preferably 0.001 to 0.1 w/v %. In particular, the total proportion of the oil component or the grease component is preferably 0.005 to 0.1 w/v %, most preferably 0.01 to 0.1 w/v %. Where Component (B) is the polyethylene glycol, the total proportion of the polyethylene glycol is preferably 0.001 to 10 w/v %, more preferably 0.005 to 5 w/v %, further preferably 0.01 to 3 w/v %, particularly preferably 0.05 to 1 w/v %. These ranges of the proportion of Component (B) are preferred for remarkably ensuring the effects of the present disclosure.

The ratio between the proportion of Component (A) and the proportion of Component (B) is not particularly limited, but depends on the types of Component (A) and Component (B). For example, the total proportion of Component (B) is typically 0.0001 to 10000 parts by mass, preferably 0.0005 to 1000 parts by mass, more preferably 0.001 to 500 parts by mass, further preferably 0.005 to 100 parts by mass, based on 1 part by mass of Component (A) contained in the inventive ophthalmic composition.

Where Component (B) is the oil component or the grease component, the total proportion of Component (B) is typically 0.0001 to 1000 parts by mass, preferably 0.0005 to 500 parts by mass, more preferably 0.001 to 100 parts by mass, further preferably 0.005 to 50 parts by mass, furthermore preferably 0.005 to 10 parts by mass, particularly preferably 0.01 to 1 part by mass, most preferably 0.05 to 1 part by mass, based on 1 part by mass of Component (A) contained in the inventive ophthalmic composition. Where Component (B) is the polyethylene glycol, the total proportion of Component (B) is typically 0.001 to 10000 parts by mass, preferably 0.005 to 1000 parts by mass, more preferably 0.01 to 500 parts by mass, further preferably 0.05 to 100 parts by mass, based on 1 part by mass of Component (A) contained in the inventive ophthalmic composition.

The inventive ophthalmic composition preferably further contains an amino acid compound for further improvement of the effects of the present disclosure. The amino acid compound herein means a compound having an amino group and a carboxyl group or a sulfo group in its molecule, or a derivative thereof. Specific examples of the amino acid compound include amino acids and mucopolysaccharides, and salts thereof. Examples of the amino acids and the salts thereof as the amino acid compound include: monoamino monocarboxylic acids such as glycine, alanine, γ-aminobutyric acid and γ-aminovaleric acid; monoamino dicarboxylic acids such as aspartic acid and glutamic acid, and salts thereof; diamino monocarboxylic acids such as arginine and lysine, and salts thereof; and aminoethylsulfonic acid (taurine) and derivatives thereof, and salts thereof. The amino acids and the amino acid salts may each be in an L-form, a D-form or a DL-form. For example, potassium L-aspartate, magnesium L-aspartate and an equimolecular mixture of potassium L-aspartate and magnesium L-aspartate are usable. Examples of the mucopolysaccharides and derivatives thereof, and the salts thereof as the amino acid compound include acidic mucopolysaccharides such as chondroitin sulfuric acid, hyaluronic acid and alginic acid, derivatives thereof, and salts thereof. The salts of the amino acids and the salts of the mucopolysaccharides include pharmaceutically, pharmacologically and physiologically acceptable salts of the amino acids and the mucopolysaccharides. Examples of such salts include: salts of organic acids such as monocarboxylic acid salts (e.g., acetates, trifluoroacetates, butyrates, paltimates, stearates and the like), polycarboxylic acid salts (e.g., fumarates, maleates and the like), hydroxycarboxylic acid salts (e.g., lactates, tartrates, citrates, succinates, malonates and the like) and organic sulfonic acid salts (e.g., methanesulfonates, toluenesulfonates and the like); salts of inorganic acids (e.g., hydrochlorides, sulfates, nitrates, hydrobromides, phosphates and the like); salts of organic bases (e.g., methylamine, triethylamine, triethanolamine, morpholine, piperazine, pyrrolidine, tripyridine, picoline and the like); and salts of inorganic bases such as ammonium salts, alkali metal salts (e.g., sodium salts, potassium salts and the like), alkali earth metal salts (e.g., calcium salts, magnesium salts and the like), aluminum salts and other metal salts, which are properly selected depending on the compound. In the case of salts of the monoamino dicarboxylic acids, for example, the inorganic base salts are preferred, and the alkali metal salts and the alkali earth metal salts are particularly preferred.

Among these amino acid compounds, potassium aspartate, aminoethylsulfonic acid and the mucopolysaccharides are preferred, and the mucopolysaccharides are more preferred. Further, sodium chondroitin sulfate and sodium hyaluronate are more preferred, and sodium chondroitin sulfate is particularly preferred.

The proportion of the amino acid compound to be contained is not particularly limited, but may be properly determined depending on the type of the amino acid compound and the types and the proportions of Component (A) and Component (B) to be used in combination with the amino acid compound. For example, the total proportion of the amino acid compound is preferably 0.01 to 7.5 w/v %, more preferably 0.02 to 5 w/v %, further preferably 0.05 to 3 w/v %, particularly preferably 0.1 to 2 w/v %, based on the total amount of the inventive ophthalmic composition. These ranges of the proportion of the amino acid compound are preferred for more remarkably ensuring the effects of the present disclosure.

The inventive ophthalmic composition preferably further contains a refreshing agent for further improvement of the effects of the present disclosure. The refreshing agent is not particularly limited, as long as it is capable of imparting the ophthalmic composition with a refreshing effect. Examples of the refreshing agent include terpenoids, and essential oils containing terpenoids (e.g., eucalyptus oil, bergamot oil, peppermint oil, fennel oil, rose oil, cinnamon oil, spearmint oil, camphor oil, cool mint, mint oil and the like). Examples of the terpenoids include menthol, menthone, camphor (also referred to as "Shono"), borneol (also referred to as "Ryuno"), geraniol, nerol, cineol, citronellol, carvone, anethole, eugenol, limonene, linalool and linalyl acetate. The terpenoids may be in a d-form, an l-form or a dl-form. Specific examples of the terpenoids include l-menthol, d-menthol, dl-menthol, dl-camphor, d-camphor, dl-borneol and d-borneol. In order to more remarkably ensure the effects of the present disclosure, menthol, camphor, borneol, geraniol and mint oil are preferred, and l-menthol, d-camphor, dl-camphor and dl-borneol are more preferred. Further, l-menthol is particularly preferred.

The proportion of the refreshing agent to be contained is not particularly limited, but may be properly determined depending on the type of the refreshing agent and the types and the proportions of Component (A) and Component (B) to be used in combination with the refreshing agent. The proportion of the refreshing agent is measured as the proportion of the terpenoid. For example, the total proportion of the refreshing agent (terpenoid) is preferably 0.00002 to 0.3 w/v %, more preferably 0.0001 to 0.1 w/v %, further preferably 0.0005 to 0.05 w/v %, particularly preferably 0.001 to 0.02 w/v %, based on the total amount of the inventive ophthalmic composition. These ranges of the proportion of the refreshing agent are preferred for more remarkably ensuring the effects of the present disclosure.

The inventive ophthalmic composition preferably further contains a nonionic surfactant for further improvement of the effects of the present disclosure. The nonionic surfactant is not particularly limited, as long as it is medically, pharmacologically (pharmaceutically) and physiologically acceptable.

Specific examples of the nonionic surfactant to be used for the inventive ophthalmic composition include POE sorbitan fatty acid esters such as POE (20) sorbitan monolaurate (Polysorbate 20), POE (20) sorbitan monopalmitate (Polysorbate 40), POE (20) sorbitan monostearate (Polysorbate 60), POE (20) sorbitan tristearate (Polysorbate 65) and POE (20) sorbitan monooleate (Polysorbate 80); POE hydrogenated castor oils such as POE (40) hydrogenated castor oil (polyoxyethylene hydrogenated castor oil 40) and POE (60) hydrogenated castor oil (polyoxyethylene hydrogenated castor oil 60); POE castor oils such as POE (10) castor oil (polyoxyethylene castor oil 10) and POE (35) castor oil (polyoxyethylene castor oil 35); POE alkyl ethers such as POE (9) lauryl ether; POE-POP alkyl ethers such as POE (20) POP (4) cetyl ether; polyoxyethylene-polyoxypropylene glycols such as POE (20) POP (20) glycol (Pluronic L44), POE (42) POP (67) glycol (Poloxamer 403 and Pluronic P123), POE (54) POP (39) glycol (Poloxamer 235 and Pluronic P85), POE (120) POP (40) glycol (Pluronic F87), POE (160) POP (30) glycol (Poloxamer 188 and Pluronic F68), POE (196) POP (67) glycol (Poloxamer 407 and Pluronic F127) and POE (200) POP (70) glycol; and polyethylene glycol monostearates such as polyoxyl 40 stearate. In the aforementioned compounds, parenthesized numerals each represent the molar number of an added alkylene oxide.

These nonionic surfactants may be used alone or in combination. Among these nonionic surfactants, the POE sorbitan fatty acid esters, the POE hydrogenated castor oils, the POE castor oils, the polyethylene glycol monostearates and the POE-POP glycols are preferred, and Polysorbate 80, POE hydrogenated castor oil 40, POE hydrogenated castor oil 60, POE castor oil 10, POE castor oil 35, polyoxyl 40 stearate, Poloxamer 188 and Poloxamer 407 are more preferred. Polysorbate 80, POE hydrogenated castor oil 40, POE hydrogenated castor oil 60 and Poloxamer 407 are further preferred.

Where the inventive ophthalmic composition contains the nonionic surfactant, the proportion of the nonionic surfactant may be properly determined depending on the type of the nonionic surfactant, the types and the proportions of the other components, and the use purpose, the formulation and the use method of the ophthalmic composition. For example, the total proportion of the nonionic surfactant is preferably 0.001 to 3 w/v %, more preferably 0.005 to 2 w/v %, further preferably 0.01 to 1 w/v %, particularly preferably 0.05 to 1 w/v %, based on the total amount of the inventive ophthalmic composition.

The inventive ophthalmic composition preferably further contains a polyhydric alcohol other than Component (B) for further improvement of the effects of the present disclosure. Examples of the polyhydric alcohol other than Component (B) include propylene glycol and glycerin. In order to more remarkably ensure the effects of the present disclosure, propylene glycol is preferred as the polyhydric alcohol other than Component (B). Commercially available products are usable as the polyhydric alcohol other than Component (B). These polyhydric alcohols may be used alone or in combination.

The proportion of the polyhydric alcohol other than Component (B) to be used for the inventive ophthalmic composition is not particularly limited, but may be properly determined depending on the type of the polyhydric alcohol, the types and the proportions of the other components, and the use purpose and the formulation of the ophthalmic composition. In order to more remarkably ensure the effects of the present disclosure, the total proportion of the polyhydric alcohol other than Component (B) is preferably 0.01 to 5 w/v %, more preferably 0.05 to 2 w/v %, further preferably 0.1 to 1 w/v %, particularly preferably 0.1 to 0.5 w/v %, based on the total amount of the ophthalmic composition.

The inventive ophthalmic composition preferably further contains an antiseptic agent for further improvement of the effects of the present disclosure. Examples of the antiseptic agent include alkyldiaminoethylglycine hydrochloride, sodium benzoate, ethanol, benzalkonium chloride, benzethonium chloride, chlorhexidine gluconate, chlorobutanol, sorbic acid, potassium sorbate, sodium dehydroacetate, methyl parahydroxybenzoate, ethyl parahydroxybenzoate, propyl parahydroxybenzoate, butyl parahydroxybenzoate, oxyquinoline sulfate, phenethyl alcohol, benzyl alcohol, alexidine, polyhexanide hydrochloride, polidronium chloride and Glokill (available from Rhodia Co., Ltd.) Commercially available products are usable as the antiseptic agent.

For further improvement of the effects of the present disclosure, alkyldiaminoethylglycine hydrochloride, benzalkonium chloride, benzethonium chloride, chlorhexidine gluconate, chlorobutanol, sorbic acid, potassium sorbate, sodium dehydroacetate, methyl parahydroxybenzoate, ethyl parahydroxybenzoate, propyl parahydroxybenzoate, butyl parahydroxybenzoate, alexidine and polyhexanide hydrochloride are preferred, and alkyldiaminoethylglycine hydrochloride, benzalkonium chloride, chlorhexidine gluconate, chlorobutanol, sorbic acid, potassium sorbate, methyl parahydroxybenzoate, ethyl parahydroxybenzoate, propyl parahydroxybenzoate, butyl parahydroxybenzoate and polyhexanide hydrochloride are more preferred among these antiseptic agents. Alkyldiaminoethylglycine hydrochloride, benzalkonium chloride, chlorhexidine gluconate and polyhexanide hydrochloride are further preferred, and benzalkonium chloride, chlorhexidine gluconate and polyhexanide hydrochloride are furthermore preferred. Polyhexanide hydrochloride is particularly preferred. These antiseptic agents may be used alone or in combination.

The proportion of the antiseptic agent to be used for the inventive ophthalmic composition is properly determined depending on the type and the molecular weight of the antiseptic agent. For further improvement of the effects of the present disclosure, for example, the total proportion of the antiseptic agent is typically 0.0000001 to 0.5 w/v %, preferably 0.0000001 to 0.2 w/v %, more preferably 0.000001 to 0.05 w/v %, further preferably 0.00001 to 0.01 w/v %, based on the total amount of the ophthalmic composition.

Where polyhexanide hydrochloride is used as the antiseptic agent, for example, the proportion of polyhexanide hydrochloride is typically 0.0000001 to 0.001 w/v %, preferably 0.000001 to 0.0005 w/v %, more preferably 0.00001 to 0.0001 w/v %, based on the total amount of the ophthalmic composition because the effects of the present disclosure are more remarkably ensured.

For further improvement of the effects of the present disclosure, the inventive ophthalmic composition preferably further contains a buffering agent. This more remarkably ensures the effects of the present disclosure. The buffering agent is not particularly limited, as long as it is medically, pharmacologically (pharmaceutically) and physiologically acceptable. Examples of the buffering agent include a boric acid buffering agent, a phosphoric acid buffering agent, a carbonic acid buffering agent, a citric acid buffering agent, an acetic acid buffering agent and a TRIS buffering agent, which may be used alone or in combination. Examples of the boric acid buffering agent include boric acid and borates (borates of alkali metals, borates of alkali earth metals and the like). Examples of the phosphoric acid buffering agent include phosphoric acid and phosphates (phosphates of alkali metals, phosphates of alkali earth metals and the like). Examples of the carbonic acid buffering agent include carbonic acid and carbonates (carbonates of alkali metals, carbonates of alkali earth metals and the like). Examples of the citric acid buffering agent include citric acid and citrates (citrates of alkali metals, citrates of alkali earth metals and the like). Examples of the acetic acid buffering agent include acetic acid and acetates (acetates of alkali metals, acetates of alkali earth metals and the like). Hydrates of the borates, the phosphates, the carbonates, the citrates and the acetates are also usable as the boric acid buffering agents, the phosphoric acid buffering agents, the carbonic acid buffering agents, the citric acid buffering agents and the acetic acid buffering agents. Specific examples of the boric acid buffering agents include boric acid and borates such as sodium borate, potassium tetraborate, potassium metaborate, ammonium borate and borax. Specific examples of the phosphoric acid buffering agents include phosphoric acid and phosphates such as disodium hydrogen phosphate, sodium dihydrogen phosphate, potassium dihydrogen phosphate, trisodium phosphate, tripotassium phosphate, calcium monohydrogen phosphate and calcium dihydrogen phosphate. Specific examples of the carbonic acid buffering agents include carbonic acid and carbonates such as sodium hydrogen carbonate, sodium carbonate, ammonium carbonate, potassium carbonate, calcium carbonate, potassium hydrogen carbonate and magnesium carbonate. Specific examples of the citric acid buffering agents include citric acid and citrates such as sodium citrate, potassium citrate, calcium citrate, sodium dihydrogen citrate and disodium citrate. Specific examples of the acetic acid buffering agents include acetic acid and acetates such as ammonium acetate, potassium acetate, calcium acetate and sodium acetate. Among these buffering agents, the boric acid buffering agents (e.g., a combination of boric acid and borax, and the like) and the phosphoric acid buffering agents (e.g., a combination of disodium hydrogen phosphate and sodium dihydrogen phosphate, and the like) are preferred, and the boric acid buffering agents are more preferred.

Where the inventive ophthalmic composition contains the buffering agent, the proportion of the buffering agent is properly determined depending on the type of the buffering agent, and the types and the proportions of the other components. The total proportion of the buffering agent is preferably 0.01 to 10 w/v %, more preferably 0.05 to 5 w/v %, further preferably 0.1 to 3 w/v %, particularly preferably 0.5 to 2 w/v %, based on the total amount of the inventive ophthalmic composition.

The inventive ophthalmic composition may contain a thickening agent other than Component (A) and Component (B), as long as the effects of the present disclosure are not impaired. Examples of the thickening agent include polyvinyl alcohols (fully or partially saponified polyvinyl alcohols), polyvinyl pyrrolidones (K25 and K30), carboxyvinyl polymers, cellulose derivatives such as methyl cellulose, ethyl cellulose, hydroxyethyl cellulose, hydroxypropyl cellulose, hydroxypropylmethyl celluloses (hypromellose, 2208, 2906, 2910 and the like), carboxymethyl cellulose, carboxyethyl cellulose, nitrocellulose and salts of these celluloses, gum arabic, tragacanth, and dextrans (40, 70 and the like). The polyvinyl alcohols (fully or partially saponified polyvinyl alcohols), the polyvinyl pyrrolidones (K25 and K30), the carboxyvinyl polymers, the cellulose derivatives and the dextran (70) are preferred, and the cellulose derivatives are more preferred. Further, hydroxyethyl cellulose and hydroxypropylmethyl celluloses are preferred, and hydroxypropylmethyl cellulose 2208, hydroxypropylmethyl cellulose 2906 and hydroxypropylmethyl cellulose 2910 are more preferred. Hydroxypropylmethyl cellulose 2906 is particularly preferred. These thickening agents may be used alone or in combination.

Where the inventive ophthalmic composition contains the thickening agent, the proportion of the thickening agent to be contained is properly determined depending on the type of the thickening agent, and the types and the proportions of the other components. The total proportion of the thickening agent is preferably 0.0001 to 5 w/v %, more preferably 0.0001 to 1 w/v %, further preferably 0.0005 to 0.5 w/v %, particularly preferably 0.001 to 0.2 w/v %, based on the total amount of the inventive ophthalmic composition.

The inventive ophthalmic composition may further contain an isotonizing agent. The isotonizing agent is not particularly limited, as long as it is medically, pharmacologically (pharmaceutically) and physiologically acceptable. Specific examples of the isotonizing agent include potassium chloride, calcium chloride, sodium chloride, magnesium chloride, sodium thiosulfate, magnesium sulfate, glucose, xylitol, mannitol and sorbitol. Among these isotonizing agents, sodium chloride, potassium chloride, calcium chloride and magnesium chloride are preferred. These isotonizing agents may be used alone or in combination.

Where the inventive ophthalmic composition contains the isotonizing agent, the proportion of the isotonizing agent to be contained is properly determined depending on the type of the isotonizing agent, and the types and the proportions of the other components. The total proportion of the isotonizing agent is preferably 0.01 to 10 w/v %, more preferably 0.05 to 5 w/v %, further preferably 0.1 to 3 w/v %, particularly preferably 0.1 to 1 w/v %, based on the total amount of the inventive ophthalmic composition.

The pH of the inventive ophthalmic composition is not particularly limited, as long as the pH falls within a medically, pharmacologically (pharmaceutically) and physiologically acceptable range. For example, the pH of the ophthalmic composition is preferably 4.0 to 9.5, more preferably 5.0 to 9.0, further preferably 5.5 to 8.5.

The osmotic pressure of the inventive ophthalmic composition is not particularly limited, as long as the osmotic pressure falls within a biologically acceptable range. For example, the osmotic pressure ratio of the ophthalmic composition is preferably 0.5 to 5.0, more preferably 0.6 to 3.0, further preferably 0.7 to 2.0, particularly preferably 0.9 to 1.55. The osmotic pressure may be adjusted by a method known in the art by using an inorganic salt, a polyhydric alcohol, a sugar alcohol, a sugar or the like. The osmotic pressure ratio is the ratio of the osmotic pressure of a sample with respect to 286 mOsm (the osmotic pressure of a 0.9 w/v % sodium chloride aqueous solution) determined based on the Japanese Pharmacopoeia, Sixteenth Edition, and the osmotic pressure is measured with reference to "Osmotic Pressure Determination (freezing-point depression method)" described in the Japanese Pharmacopoeia. The standard solution (0.9 w/v % sodium chloride aqueous solution) for the determination of the osmotic pressure ratio may be prepared by weighing exactly 0.900 g of sodium chloride (Japanese Pharmacopoeia standard reagent) dried at 500° C. to 650° C. for 40 to 50 minutes and allowed to cool in a desiccator (with silica gel), and dissolving the weighed sodium chloride in purified water exactly to a volume of 100 mL, or a commercially available standard solution (0.9 w/v % sodium chloride aqueous solution) for the determination of the osmotic pressure ratio may be used.

The viscosity of the inventive ophthalmic composition is not particularly limited, as long as the viscosity falls within a biologically acceptable range. For example, the viscosity of the ophthalmic composition is preferably 0.1 to 1000 mPa·s, more preferably 0.5 to 100 mPa·s, further preferably 1 to 50 mPa·s, particularly preferably 1 to 10 mPa·s, as measured at 25° C. by means of a rotational viscometer (VISCOMETER MODEL RE550 available from Toki Sangyo Co., Ltd., and having a rotor (1°34'×R24)).

The inventive ophthalmic composition may contain various pharmacologically active components or physiologically active components in proper amounts in addition to the aforementioned components, as long as the effects of the present disclosure are not impaired. These components are not particularly limited, but examples thereof include effective components to be generally used in various medicaments as described in Standards for Marketing Approval of Nonprescription Drugs 2012 (supervised by Society for Regulatory Science of Medical Products). Specific examples of effective components to be used in ophthalmic medicaments are as follows:

Antihistamines such as iproheptine, diphenhydramine, chlorpheniramine maleate, ketotifen fumarate, olopatadine hydrochloride and levocabastine hydrochloride;

Antiallergic agents such as sodium cromoglicate, tranilast and pemirolast potassium;

Steroids such as fluticasone propionate, fluticasone furoate, mometasone furoate, beclomethasone propionate and flunisolide;

Vasoconstrictors such as tetrahydrozoline hydrochloride, tetrahydrozoline nitrate, naphazoline hydrochloride, naphazoline nitrate, epinephrine, epinephrine hydrochloride, ephedrine hydrochloride, phenylephrine hydrochloride and dl-methylephedrine hydrochloride;

Ocular muscle modulating agents such as a cholinesterase inhibitor having an active center similarly to acetylcholine, specifically neostigmine methylsulfate, tropicamide, helenien and atropine sulfate;

Anti-inflammatory agents such as glycyrrhetic acid, glycyrrhizic acid, pranoprofen, methyl salicylate, glycol salicylate, allantoin, tranexamic acid, ε-aminocaproic acid, berberine, sodium azulene sulfonate, lysozyme and licorice;

Astringents such as zinc white, zinc lactate and zinc sulfate;

Vitamins such as flavin adenine dinucleotide sodium, cyanocobalamin, pyridoxine hydrochloride, panthenol, calcium pantothenate, sodium pantothenate, retinol acetate, retinol palmitate and tocopherol acetate;

Local anesthetics such as lidocaine; and other agents such as sulfamethoxazole and sulfamethoxazole sodium.

The inventive ophthalmic composition may further contain various excipients in proper proportions in an ordinary manner depending on the use purpose and the formulation of the ophthalmic composition, as long as the effects of the present disclosure are not impaired. These excipients may be used alone or in combination. Examples of the excipients are described in Japanese Pharmaceutical Excipients Directory 2007 (edited by International Pharmaceutical Excipients Council Japan). Typical examples of the excipients are as follows:

Carriers such as water, hydrous ethanol and other aqueous carriers;

Saccharides such as cyclodextrin;

Stabilizers such as sodium formaldehyde sulfoxylate (Rongalite), tocopherol, sodium pyrosulfite, monoethanolamine, aluminum monostearate, glycerin monostearate, dibutylhydroxytoluene, sodium edetate, sodium hydrogen sulfite and sodium sulfite; and Anionic surfactants such as alkylbenzenesulfonates, alkyl sulfates, polyoxyethylene alkyl sulfates, α-sulfo-fatty acid esters and α-olefin sulfonic acids.

The inventive ophthalmic composition is prepared by adding desired proportions of Component (A) and Component (B) described above and, as required, other optional components to a carrier. Medically, pharmacologically (pharmaceutically) and physiologically acceptable water is usable as the carrier. Specific examples of the water include distilled water, common water, purified water, sterile purified water and distilled water for injection.

These components are dissolved or dispersed, for example, in purified water, and the resulting solution or dispersion is conditioned to a predetermined pH and a predetermined osmotic pressure and sterilized by a filtration sterilization method or the like. Thus, the inventive ophthalmic composition is prepared.

In the inventive ophthalmic composition, water is present in a proportion of not less than 85 w/v %, preferably not less than 90 w/v %, more preferably not less than 92 w/v %, further preferably not less than 94 w/v %, particularly preferably not less than 96 w/v %, based on the total amount of the ophthalmic composition.

The ophthalmic composition according to this embodiment may be provided in various formulations according to the use purpose thereof. Exemplary formulations include a liquid form, a gel form and a semisolid form (ointment or the like). The ophthalmic composition according to this embodiment is preferably in the liquid form.

The inventive ophthalmic composition is contained in any container. The container for containing the inventive ophthalmic composition is not particularly limited but, for example, may be made of a glass material or a plastic material. Preferably, the container is made of the plastic material. Examples of the plastic material include polyethylene terephthalate, polyarylate, polyethylene naphthalate, polycarbonate, polyethylene, polypropylene and polyimide, copolymers of monomers for any of these polymers, and blends of any of these polymers. The polyethylene terephthalate is preferred. The container for containing the inventive ophthalmic composition may be a transparent container through which its inside is visible, or may be an opaque container through which its inside is hardly visible. The transparent container is preferred. The term "transparent container" herein means both a colorless transparent container and a colored transparent container. The inventive ophthalmic composition may be contained, for example, in a repeatedly usable multi-dose form in a colored transparent plastic container or the like for use. Alternatively, the ophthalmic composition may be contained in a unit-dose form for use.

The inventive ophthalmic composition may be used as a pharmaceutical product or a quasi-pharmaceutical product, and examples of the pharmaceutical product and the quasi-pharmaceutical product include so-called eyedrops (including eyedrops which can be instilled into eyes during wearing of contact lenses), artificial lacrimal fluids, eyewash solutions (including eyewash solutions which can be used for washing eyes during wearing of contact lenses) and compositions for contact lenses such as contact lens wetting solutions, contact lens care compositions (contact lens sterilization solutions, contact lens storage solutions, contact lens cleaning solutions, contact lens cleaning/storage solutions and contact lens sterilization/cleaning/storage solutions (multi-purpose solutions) and the like). In the present disclosure, the eyedrops, the artificial lacrimal fluids, the eyewash solutions and the contact lens wetting solutions are preferred, and the eyedrops and the artificial lacrimal fluids are particularly preferred. Where the ophthalmic composition is used for contact lenses, the ophthalmic composition can be applied to any types of contact lenses including hard contact lenses and soft contact lenses (including ionic contact lenses and nonionic contact lenses, and hydrogel contact lenses such as silicone hydrogel contact lenses and non-silicone hydrogel contact lenses).

In this embodiment, the ophthalmic composition has a more remarkable friction reducing effect for reducing friction occurring between the contact lenses and conjunctivae or between the contact lenses and corneas during the wearing of the contact lenses. Therefore, the ophthalmic composition is preferably adapted for the contact lenses, and particularly preferably adapted for the soft contact lenses. Of the soft contact lenses, the silicone hydrogel contact lenses each have a greater surface friction and, particularly, color contact lenses having color print, pattern print or the like on surfaces thereof each have a greater surface friction than the other hydrogel contact lenses. Therefore, the inventive ophthalmic composition is particularly preferably an ophthalmic composition for the silicon hydrogel contact lenses or an ophthalmic composition for the color contact lenses.

The ophthalmic composition according to this embodiment is expected to have an eye strain alleviating effect in addition to the friction reducing effect and the sticky sensation alleviating effect when the ophthalmic composition is instilled in eyes.

[2. Reduction of Friction]

The inventive ophthalmic composition is smooth with a reduced frictional resistance with respect to objects to be brought into contact with the ophthalmic composition (conjunctivae (including lid margin conjunctivae or lid wipers), corneas and contact lenses (each having a front surface to be exposed to the outside during the wearing thereof, a back surface to be kept in contact with an eyeball during the wearing thereof and a peripheral edge portion) and the like), and alleviates an uncomfortable sensation in the blinking of the eyes and during the wearing of the contact lenses, thereby ensuring an excellent use sensation. According to another embodiment of the present disclosure, the ophthalmic composition containing the polyvinyl pyrrolidone K90 (Component (A)) and at least one (Component (B)) selected from the group consisting of the oil component, the grease component and the polyethylene glycol is provided as a friction reducing agent (preferably for reducing the friction during the wearing of the contact lenses).

According to further another embodiment of the present disclosure, the polyvinyl pyrrolidone K90 (Component (A)) and at least one (Component (B)) selected from the group consisting of the oil component, the grease component and the polyethylene glycol are used in combination for production of the ophthalmic composition having the friction reducing effect (preferably for reducing the friction during the wearing of the contact lenses). According to still another embodiment of the present disclosure, there is provided a method for imparting an ophthalmic composition with the friction reducing effect (preferably for reducing the friction during the wearing of the contact lenses), the method including the step of adding the polyvinyl pyrrolidone K90 (Component (A)) and at least one (Component (B)) selected from the group consisting of the oil component, the grease component and the polyethylene glycol to the ophthalmic composition. According to further another embodiment of the present disclosure, there is provided a method for reducing the friction during the wearing of the contact lenses, the method including the step of applying the ophthalmic composition containing the polyvinyl pyrrolidone K90 (Component (A)) and at least one (Component (B)) selected from the group consisting of the oil component, the grease component and the polyethylene glycol to the contact lenses. In this method, the ophthalmic composition may be applied to the contact lenses during the wearing of the contact lenses or when the contact lenses are put on eyes.

In the present disclosure, at least one of Component (A) and Component (B) may be contained as an effective component in the ophthalmic composition.

EXAMPLES

The present disclosure will be described in detail by way of inventive examples and comparative examples for each evaluation test, but is not limited by these examples.

In Tables 1 to 5, the amounts of the respective components are expressed in a unit of w/v %.

Test Example 1: Sticky Sensation Evaluation

Examples 1 and Comparative Example 1

Ophthalmic compositions were respectively prepared according to formulations (Examples 1-1 and 1-2, and Comparative Example 1-1) shown below in Table 1, and 13 mL of each of the ophthalmic compositions was aseptically filled in an eyedrop container of polyethylene terephthalate having a volume of 14.2 mL. After the filling, a polyethylene nozzle was attached to the eyedrop container. Four panelists with naked eyes instilled each of the ophthalmic compositions into right and left eyes and, immediately thereafter, evaluated the ophthalmic compositions for sticky sensation in the following manner based on VAS (visual analog scale) to determine a sticky sensation alleviating rate (%). The results are also shown below in Table 1. In the present disclosure, the term "sticky sensation" means a sticky and filmy sensation which is different from "viscous sensation" often caused due to the viscosity of an ophthalmic composition attributable to the presence of saccharides such as cellulose.

<Sticky Sensation Evaluation Method>

On a 100-mm line scale ranging from 0 mm (indicating no sticky sensation) to 100 mm (indicating a strong sticky sensation) in a symptom survey sheet, the panelists each placed a mark to indicate how strong the sticky sensation was. The lengths (mm) were employed as VAS scores. That is, a higher VAS score means a higher sticky sensation score. The VAS scores were averaged, and the sticky sensation alleviating rate with respect to the sticky sensation of Comparative Example 1-1 was calculated from the following expression (2):

Sticky sensation alleviating rate (%)=(Average score for Comparative Example 1-1−Average score for Each Example)/Average score for Comparative Example 1-1×100 . . . (2)

TABLE 1

| | Comparative Example 1-1 | Example 1-1 | Example 1-2 |
|---|---|---|---|
| Polyvinyl pyrrolidone K90 | 0.05 | 0.05 | 0.05 |

TABLE 1-continued

| | Comparative Example 1-1 | Example 1-1 | Example 1-2 |
|---|---|---|---|
| Polyethylene glycol 400 | — | 1 | — |
| Sesame oil | — | — | 0.1 |
| Polysorbate 80 | — | — | 1 |
| Boric acid | 1.5 | 1.5 | 1.5 |
| Borax | 0.125 | 0.125 | 0.125 |
| Hydrochloric acid/ sodium hydroxide | Proper amount | Proper amount | Proper amount |
| Purified water | Balance | Balance | Balance |
| pH | 7 | 7 | 7 |
| Sticky sensation alleviating rate (%) | — | 52.9 | 44.5 |

The results shown in Table 1 indicate that, where Component (A) and Component (B) are used in combination for the ophthalmic composition, the eye sticky sensation after the instillation of the ophthalmic composition tends to be unexpectedly significantly alleviated as compared with the ophthalmic composition containing only Component (A) out of Components (A) and (B).

Test Example 2: Friction Evaluation

Examples 2 and Comparative Examples 2

A soft contact lens (available under the trade name of PROCLEAR 1-DAY (Omafilcon A) from Coopervision Company and classified in a soft contact lens classification group II as specified by the U.S. Food and Drug Administration (FDA)) was rinsed with a phosphate buffered saline solution (containing 0.83 w/v % sodium chloride, 0.5993 w/v % sodium hydrogen phosphate dodecahydrate and 0.0528 w/v % sodium dihydrogen phosphate dihydrate). After unnecessary liquid was wiped from surfaces of the soft contact lens, the soft contact lens was soaked in each of ophthalmic compositions (Examples 2-1 and 2-2, and Comparative Examples 2-1, 2-2, 2-3, 2-4 and 2-5) respectively having formulations shown below in Table 2 for 10 seconds. Then, the soft contact lens was bonded to a contactor of a frictional sensation tester (Tribomaster TL201Ts available from Trinity Laboratories Ltd.) On the other hand, an artificial skin soaked in a saline solution for 1 hour was stuck on a movable table of the frictional sensation tester, and 4 mL of the saline solution was spread over a contactor movable range on the artificial skin. Then, 20 g weight was attached to a measurement unit. The contactor to which the soft contact lens was bonded was mounted on the measurement unit, and measurement was performed 100 times per second for 20 seconds. Dynamic friction coefficient values obtained for each of the ophthalmic compositions through the measurement during a period from 5 seconds to 20 seconds after the start of the measurement were averaged, and the average dynamic friction coefficient was defined as the dynamic friction coefficient ($\mu k$) of the ophthalmic composition. The rate of reduction in dynamic friction coefficient with respect to the dynamic friction coefficient of an ophthalmic composition of Reference Example shown below in Table 2 was calculated from the following expression (3), and defined as the friction reduction rate (%) of the ophthalmic composition. The results are also shown below in Table 2. Further, a bar graph showing the friction reduction rates (%) of Examples 2-1 and 2-2 and Comparative Examples 2-1, 2-2, 2-3, 2-4 and 2-5 with respect to Reference Example along the vertical axis was made and shown in FIG. 1.

Friction reduction rate (%)=(Friction coefficient of Reference Example−Dynamic friction coefficient of each of Ophthalmic compositions)/Dynamic friction coefficient of Reference Example×100 . . . (3)

TABLE 2

|  | Reference Example | Comparative Example 2-1 | Comparative Example 2-2 | Comparative Example 2-3 | Example 2-1 | Example 2-2 | Comparative Example 2-4 | Comparative Example 2-5 |
|---|---|---|---|---|---|---|---|---|
| Polyvinyl pyrrolidone K90 | — | 0.05 | — | — | 0.05 | 0.05 | — | — |
| Polyvinyl pyrrolidone K25 | — | — | — | — | — | — | 0.05 | 0.05 |
| Polyethylene glycol 400 | — | — | 1 | — | 1 | — | 1 | — |
| Sesame oil | — | — | — | 0.1 | — | 0.1 | — | 0.1 |
| Polysorbate 80 | — | — | — | 1 | — | 1 | — | 1 |
| Boric acid | 1.5 | 1.5 | 1.5 | 1.5 | 1.5 | 1.5 | 1.5 | 1.5 |
| Borax | 0.125 | 0.125 | 0.125 | 0.125 | 0.125 | 0.125 | 0.125 | 0.125 |
| Hydrochloric acid/ sodium hydroxide | Proper amount | Proper amount | Proper amount | Proper amount | Proper amount | Proper amount | Proper amount | Proper amount |
| Purified water | Balance | Balance | Balance | Balance | Balance | Balance | Balance | Balance |
| pH | 7 | 7 | 7 | 7 | 7 | 7 | 7 | 7 |
| Friction reduction rate (%) | — | 4.42 | 0.18 | 0.0 | 10.27 | 18.52 | 6.07 | 5.66 |

The results shown in Table 2 and the graph of FIG. 1 indicate that the ophthalmic compositions of Comparative Examples 2-2 and 2-3 containing either of the sesame oil and the polyethylene glycol have almost no friction reducing effect as compared with the ophthalmic composition of Reference Example and, in contrast, the ophthalmic compositions of Examples 2-1 and 2-2 containing the polyvinyl pyrrolidone K90 and at least one of the polyethylene glycol and the sesame oil unexpectedly significantly improve the friction reduction rate as compared with the ophthalmic composition of Comparative Example 2-1 containing only the polyvinyl pyrrolidone K90 out of these components. On the other hand, the ophthalmic compositions of Comparative Examples 2-4 and 2-5 employing the polyvinyl pyrrolidone K25 instead of the polyvinyl pyrrolidone K90 do not have a significant friction reducing effect.

Test Example 3: Use Sensation Evaluation I

Example 3 and Comparative Example 3

Ophthalmic compositions (Example 3 and Comparative Example 3) were respectively prepared according to formulations shown below in Table 3, and 13 mL of each of the ophthalmic compositions was aseptically filled in an eyedrop container of polyethylene terephthalate having a volume of 14.2 mL. After the filling, a polyethylene nozzle was attached to the eyedrop container. Three panelists with naked eyes instilled one droplet of each of the ophthalmic compositions into each of right and left eyes and, thereafter, evaluated the ophthalmic compositions for plural items of use sensation in the following manner based on VAS (visual analog scale). Then, a score change rate was determined for each of the use sensation items. The results are also shown below in Table 3. It was preliminarily confirmed that there was no difference between the states of the right and left eyes of each of the panelists.

<Use Sensation Evaluation>

On a 100-mm line scale ranging from 0 mm (indicating no sticky sensation immediately after the instillation) to 100 mm (indicating strong sticky sensation) and a 100-mm line scale ranging from 0 mm (indicating no residual sensation after a lapse of 10 minutes from the instillation) to 100 mm (indicating strong residual sensation) in a symptom survey sheet, the panelists placed marks to indicate how strong these sensations were. The lengths (mm) were employed as VAS scores. That is, a lower VAS score for the sticky sensation means a lower sticky sensation score, and a higher VAS score for the residual sensation after the lapse of 10 minutes means a higher residual sensation score. The VAS scores for each of the items were averaged, and the change rates of the average scores for Example 3 with respect to the average scores for Comparative Example 3 were calculated from the following expression (4). In the evaluation for the sticky sensation, for example, the ophthalmic composition of Example 3 had a lower sticky sensation score than the ophthalmic composition of Comparative Example 3 with the sticky sensation alleviated. In the expression (4), therefore, the value of (Average score for Example−Average score for Comparative Example) had a minus sign (−) and, hence, the change rate (%) also had a minus sign (−). In the present disclosure, the term "residual sensation" means a sensation such that the ophthalmic composition remains in the eyes, and the improvement in residual sensation is effective for maintaining a desired efficacy and a refreshing sensation.

Score change rate (%)=(Average score for Example−Average score for Comparative Example)/Average score for Comparative Example×100 . . . (4)

TABLE 3

|  | Example 3 | Comparative Example 3 |
|---|---|---|
| Polyvinyl pyrrolidone K90 | 0.5 | 0.5 |
| Sesame oil | 0.1 | — |
| Polyoxyethylene castor oil 10 | 0.2 | 0.2 |
| Polyoxyl 40 monostearate | 0.15 | 0.15 |
| Calcium chloride | 0.005 | 0.005 |
| Magnesium chloride | 0.05 | 0.05 |
| l-menthol | 0.002 | 0.002 |
| Polyhexanide hydrochloride | 0.0001 | 0.0001 |
| Sodium Edetate | 0.05 | 0.05 |
| Boric acid | 1 | 1 |
| Borax | 0.1 | 0.1 |
| Hydrochloric acid | Proper amount | Proper amount |
| Sodium hydroxide | Proper amount | Proper amount |
| Purified water | Balance | Balance |
| Total amount | 100 mL | 100 mL |
| pH | 7.0 | 7.0 |
| Eye for instillation | Left eye | Right eye |
| Sticky sensation change rate (%) | −72.4 | — |
| Residual sensation change rate (%) | 19.7 | — |

The results shown above in Table 3 indicate that, where Component (A) and Component (B) are used in combination in the presence of l-menthol, polyhexanide hydrochloride and sodium edetate, the eye sticky sensation after the instillation is significantly alleviated and the eyedrop residual sensation is improved as compared with the ophthalmic composition containing only Component (A) out of Components (A) and (B).

Test Example 4: Use Sensation Evaluation II Example 4 and Comparative Example 4

Ophthalmic compositions (Example 4 and Comparative Example 4) were respectively prepared according to formulations shown below in Table 4, and 13 mL of each of the ophthalmic compositions was aseptically filled in an eyedrop container of polyethylene terephthalate having a volume of 14.2 mL. After the filling, a polyethylene nozzle was attached to the eyedrop container. Three panelists with naked eyes instilled one droplet of each of the ophthalmic compositions into each of right and left eyes and, thereafter, evaluated the ophthalmic compositions for plural items of use sensation in the following manner based on VAS (visual analog scale). Then, a score change rate was determined for each of the use sensation items. The results are also shown below in Table 4. It was preliminarily confirmed that there was no difference between the states of the right and left eyes of each of the panelists.

<Use Sensation Evaluation>

On a 100-mm line scale ranging from 0 mm (indicating no eye sticky sensation after a lapse of 10 minutes from the instillation) to 100 mm (indicating a strong sticky sensation) and a 100-mm line scale ranging from 0 mm (indicating no dry eye sensation) to 100 mm (indicating a strong dry eye sensation) in a symptom survey sheet, the panelists each placed marks to indicate how strong these sensations were. The lengths (mm) were employed as VAS scores. That is, a lower VAS score for the sticky sensation means a lower sticky sensation score, and a lower VAS score for the dry eye sensation means a lower dry eye sensation score. The VAS scores for each of the items were averaged, and the change rates of the average sensation scores for Example with respect to the average sensation scores for Comparative Example 4 were calculated from the above expression (4).

TABLE 4

|  | Example 4 | Comparative Example 4 |
| --- | --- | --- |
| Polyvinyl pyrrolidone K90 | 0.5 | 0.5 |
| Sesame oil | 0.1 | — |
| Polyoxyethylene castor oil 10 | 0.2 | 0.2 |
| Polyoxyl 40 monostearate | 0.15 | 0.15 |
| Calcium chloride | 0.005 | 0.005 |
| Magnesium chloride | 0.05 | 0.05 |
| Poloxamer 407 | 0.1 | 0.1 |
| Polyhexanide hydrochloride | 0.0001 | 0.0001 |
| Sodium Edetate | 0.05 | 0.05 |
| Boric acid | 1 | 1 |
| Borax | 0.1 | 0.1 |
| Hydrochloric acid | Proper amount | Proper amount |
| Sodium hydroxide | Proper amount | Proper amount |
| Purified water | Balance | Balance |
| Total amount | 100 mL | 100 mL |
| pH | 7.0 | 7.0 |
| Sticky sensation change rate (%) | −76.4 | — |
| Dry eye sensation change rate (%) | −45.1 | — |

The results shown in Table 4 indicate that, where Component (A) and Component (B) are used in combination in the presence of Poloxamer 407, polyhexanide hydrochloride and sodium edetate, the eye sticky sensation after the instillation is significantly alleviated and the dry eye sensation is also significantly alleviated as compared with the ophthalmic composition containing only Component (A) out of Components (A) and (B).

Test Example 5: Use Sensation Evaluation III

Example 5 and Comparative Example 5

Ophthalmic compositions (Example 5 and Comparative Example 5) were respectively prepared according to formulations shown below in Table 5, and 13 mL of each of the ophthalmic compositions was aseptically filled in an eyedrop container of polyethylene terephthalate having a volume of 14.2 mL. After the filling, a polyethylene nozzle was attached to the eyedrop container. Three panelists with naked eyes instilled one droplet of each of the ophthalmic compositions into each of right and left eyes and, thereafter, evaluated the ophthalmic compositions for plural items of use sensation in the following manner based on VAS (visual analog scale). Then, a score change rate was determined for each of the use sensation items. The results are also shown below in Table 5. It was preliminarily confirmed that there was no difference between the states of the right and left eyes of each of the panelists.

<Use Sensation Evaluation>

On a 100-mm line scale ranging from 0 mm (indicating no sticky sensation immediately after the instillation) to 100 mm (indicating a strong sticky sensation), a 100-mm line scale ranging from 0 mm (indicating lower visibility with a blurred vision sensation) to 100 mm (indicating higher visibility with no blurred vision sensation), a 100-mm line scale ranging from 0 mm (indicating no foreign body sensation) to 100 mm (indicating a strong foreign body sensation) and a 100-mm line scale ranging from 0 mm (indicating no gritty sensation) to 100 mm (indicating a strong gritty sensation) in a symptom survey sheet, the panelists each placed marks to indicate how strong these sensations were. The lengths (nm) were employed as VAS scores. That is, a lower VAS score for the sticky sensation means a lower sticky sensation score, and a higher VAS score for the visibility (insusceptibility to the blurred vision sensation) means a higher visibility score. Lower VAS scores for the foreign body sensation and the gritty sensation respectively mean a lower foreign body sensation score and a lower gritty sensation score. The VAS scores for each of the items were averaged, and the change rates of the average sensation scores for Example with respect to the average sensation scores for Comparative Example 5 were calculated from the above expression (4).

TABLE 5

|  | Example 5 | Comparative Example 5 |
| --- | --- | --- |
| Polyvinyl pyrrolidone K90 | 0.5 | 0.5 |
| Sesame oil | 0.05 | — |
| Polyoxyethylene castor oil 10 | 0.2 | 0.2 |
| Polyoxyl 40 monostearate | 0.15 | 0.15 |
| Calcium chloride | 0.005 | 0.005 |
| Magnesium chloride | 0.05 | 0.05 |
| Sodium chondroitin sulfate | 0.5 | 0.5 |
| Polyhexanide hydrochloride | 0.0001 | 0.0001 |
| Sodium Edetate | 0.05 | 0.05 |
| Boric acid | 1 | 1 |
| Borax | 0.1 | 0.1 |

TABLE 5-continued

|  | Example 5 | Comparative Example 5 |
|---|---|---|
| Hydrochloric acid | Proper amount | Proper amount |
| Sodium hydroxide | Proper amount | Proper amount |
| Purified water | Balance | Balance |
| Total amount | 100 mL | 100 mL |
| pH | 6.9 | 6.9 |
| Sticky sensation change rate (%) | −20.6 | — |
| Visibility change rate (blur-free vision change rate) (%) | 8.0 | — |
| Foreign body sensation change rate (%) | −36.0 | — |
| Gritty sensation change rate (%) | −72.4 | — |

The results shown in Table 5 indicate that, where Component (A) and Component (B) are used in combination in the presence of sodium chondroitin sulfate, polyhexanide hydrochloride, sodium edetate and the like, the eye sticky sensation after the instillation is significantly alleviated, and the blurred vision (less visible) sensation, the foreign body sensation and the gritty sensation are also significantly alleviated as compared with the ophthalmic composition containing only Component (A) out of Components (A) and (B).

Formulations 1 to 28 are shown below in Tables 6 to 11. In Tables 6 to 11, the proportions of the respective components are expressed in a unit of w/v %.

Pharmaceutical products 1 to 25 were respectively produced by filling eyedrops of Formulations 1 to 25 in polyethylene terephthalate containers and attaching polyethylene nozzles to the respective polyethylene terephthalate containers. Pharmaceutical products 26 to 50 were respectively produced by filling the eyedrops of Formulations 1 to 25 in polyethylene terephthalate containers and attaching polybutylene terephthalate nozzles to the respective polyethylene terephthalate containers. Further, a pharmaceutical product 51 was produced by filling an eyewash solution of Formulation 26 in a polyethylene terephthalate container, and a pharmaceutical product 52 was produced by filling a contact lens sterilization/cleaning/storage solution of Formulation 27 in a high-density polyethylene container. A pharmaceutical product 53 was produced by filling a contact lens wetting solution of Formulation 28 in a polyethylene terephthalate container. A pharmaceutical product 54 was produced by filling the contact lens sterilization/cleaning/storage solution of Formulation 27 in a polypropylene container, and a pharmaceutical product 55 was produced by filling the contact lens sterilization/cleaning/storage solution of Formulation 27 in a polyethylene terephthalate container.

TABLE 6

|  | Formulation 1 Eyedrop | Formulation 2 Eyedrop | Formulation 3 Eyedrop | Formulation 4 Eyedrop | Formulation 5 Eyedrop | Formulation 6 Eyedrop |
|---|---|---|---|---|---|---|
| Polyyinyl pyrrolidone R90 | 0.5 | 1 | 0.7 | 0.5 | 1 | 0.7 |
| Sesame oil | 0.2 | 0.05 | 0.1 | 0.2 | 0.05 | 0.1 |
| Propylene glycol | 0.5 | 0.2 | 0.3 | 0.5 | 0.2 | 0.3 |
| Polyoxyethylene castor oil 35 | 0.7 | 0.5 | 0.3 | — | — | — |
| Polyoxyethylene castor oil 10 | — | — | — | 0.5 | 0.6 | 0.3 |
| Polyoxyl 40 monostearate | 0.2 | 0.1 | 0.15 | 0.1 | 0.2 | 0.15 |
| Calcium chloride | 0.005 | 0.001 | 0.002 | 0.005 | 0.001 | 0.002 |
| Magnesium chloride | 0.05 | 0.01 | 0.001 | 0.05 | 0.001 | 0.01 |
| l-menthol | 0.002 | 0.005 | 0.001 | 0.002 | 0.005 | 0.001 |
| Polyhexanide hydrochloride | 0.0001 | 0.0001 | 0.0001 | 0.0001 | 0.0001 | 0.0001 |
| Sodium edetate | 0.05 | 0.04 | 0.03 | 0.05 | 0.04 | 0.03 |
| Boric acid | 1 | 1.3 | 1.5 | 1 | 1.3 | 1.5 |
| Borax | 0.1 | 0.3 | 0.2 | 0.1 | 0.3 | 0.2 |
| Hydrochloric acid | Proper amount | Proper amount | Proper amount | Proper amount | Proper amount | Proper amount |
| Sodium hydroxide | Proper amount | Proper amount | Proper amount | Proper amount | Proper amount | Proper amount |
| Purified water | Balance | Balance | Balance | Balance | Balance | Balance |
| pH | 7 | 7 | 7 | 7 | 7 | 7 |

TABLE 7

|  | Formulation 7 Eyedrop | Formulation 8 Eyedrop | Formulation 9 Eyedrop | Formulation 10 Eyedrop | Formulation 11 Eyedrop |
|---|---|---|---|---|---|
| Polyvinyl pyrrolidone K90 | 0.05 | 1 | 0.5 | 0.5 | 0.1 |
| Sesame oil | 0.05 | 0.1 | 0.2 | 0.01 | 0.01 |
| Polyethylene glycol 400 | — | — | — | — | 0.1 |
| Pyridoxine hydrochloride | — | — | — | — | 0.1 |
| Chlorpheniramine maleate | — | — | — | — | 0.03 |
| Dipotassium glycyrrhizinate | — | — | — | — | 0.25 |
| Potassium aspartate | — | 1 | — | 1 | — |
| Aminoethylsulfonic acid | — | — | 1 | 1 | — |
| Sodium chondroitin sulfate | 0.5 | 0.5 | 0.5 | 0.5 | 0.5 |
| Hydroxypropylmethyl cellulose 2906 | — | 0.1 | — | 0.1 | — |
| Hydroxyethyl cellulose | 0.3 | — | 0.3 | — | — |
| Sodium hyaluronate | 0.01 | 0.005 | 0.01 | 0.005 | — |
| Propylene glycol | — | — | — | — | 0.1 |

TABLE 7-continued

|  | Formulation 7 Eyedrop | Formulation 8 Eyedrop | Formulation 9 Eyedrop | Formulation 10 Eyedrop | Formulation 11 Eyedrop |
|---|---|---|---|---|---|
| Polysorbate 80 | 0.3 | — | 0.5 | — | — |
| Polyoxyethylene hydrogenated castor oil 60 | — | 0.3 | — | 0.3 | 0.1 |
| Sodium chloride | 0.4 | 0.5 | 0.4 | 0.5 | 0.3 |
| Potassium chloride | 0.1 | 0.1 | 0.1 | 0.1 | 0.05 |
| Calcium chloride | — | 0.005 | — | — | 0.005 |
| Magnesium chloride | — | 0.002 | — | — | 0.005 |
| l-menthol | 0.001 | 0.002 | 0.001 | 0.002 | 0.001 |
| d-camphor | 0.001 | — | 0.001 | — | — |
| d-borneol | — | — | — | — | 0.001 |
| Polyhexanide hydrochloride | 0.00005 | 0.0001 | 0.00015 | 0.0001 | 0.0001 |
| Sodium edetate | 0.05 | 0.05 | 0.05 | 0.05 | 0.05 |
| Boric acid | 1 | 0.5 | 1 | 0.5 | 1.5 |
| Borax | 0.1 | 0.03 | 0.2 | 0.03 | 0.1 |
| Hydrochloric acid | Proper amount | Proper amount | Proper amount | Proper amount | Proper amount |
| Sodium hydroxide | Proper amount | Proper amount | Proper amount | Proper amount | Proper amount |
| Purified water | Balance | Balance | Balance | Balance | Balance |
| pH | 7 | 7 | 7.5 | 6.5 | 7 |

TABLE 8

|  | Formulation 12 Eyedrop | Formulation 13 Eyedrop | Formulation 14 Eyedrop | Formulation 15 Eyedrop | Formulation 16 Eyedrop |
|---|---|---|---|---|---|
| Polyvinyl pyrrolidone K90 | 0.5 | 0.5 | 0.1 | 2 | 0.5 |
| Sesame oil | 0.05 | — | — | — | 0.1 |
| Castor oil | — | 0.05 | — | — | — |
| Polyethylene glycol 400 | — | — | 1 | 0.1 | 0.5 |
| Postassium aspartate | — | — | — | 1 | — |
| Aminoethylsulfonic acid | — | — | — | — | 1 |
| Sodium chondroitin sulfate | 0.5 | 0.5 | 0.5 | 0.5 | 0.5 |
| Hydroxypropylmethyl cellulose 2906 | — | — | — | 0.1 | — |
| Hydroxyethyl cellulose | 0.3 | 0.3 | 0.3 | — | 0.3 |
| Sodium hyaluronate | 0.01 | 0.01 | 0.01 | 0.005 | 0.01 |
| Polysorbate 80 | 0.3 | 0.3 | 0.3 | — | 0.3 |
| Polyoxyethylene hydrogenated castor oil 60 | — | — | — | 0.3 | 0.2 |
| Sodium chloride | 0.4 | 0.4 | 0.4 | 0.5 | 0.4 |
| Potassium chloride | 0.1 | 0.1 | 0.1 | 0.1 | 0.1 |
| Calcium chloride | — | — | — | 0.005 | — |
| Magnesium chloride | — | — | — | 0.002 | — |
| l-menthol | 0.001 | 0.001 | 0.001 | 0.002 | 0.001 |
| d-camphor | 0.001 | 0.001 | 0.001 | — | 0.001 |
| Polyhexanide hydrochloride | — | 0.00005 | 0.00005 | — | 0.00015 |
| Chlorohexidine gluconate | 0.005 | — | — | 0.005 | — |
| Trometamol | 0.1 | — | — | 0.1 | — |
| Sodium edetate | 0.05 | 0.05 | 0.05 | 0.05 | 0.05 |
| Boric acid | 1 | 1 | 1.5 | 0.5 | 1 |
| Borax | 0.1 | 0.1 | 0.1 | 0.03 | 0.1 |
| Hydrochloric acid | Proper amount | Proper amount | Proper amount | Proper amount | Proper amount |
| Sodium hydroxide | Proper amount | Proper amount | Proper amount | Proper amount | Proper amount |
| Purified water | Balance | Balance | Balance | Balance | Balance |
| pH | 7 | 7 | 6.5 | 7.5 | 7 |

TABLE 9

|  | Formulation 17 Eyedrop | Formulation 18 Eyedrop | Formulation 19 Eyedrop | Formulation 20 Eyedrop | Formulation 21 Eyedrop |
|---|---|---|---|---|---|
| Polyvinyl pyrrolidone K90 | 1 | 0.1 | 1 | 0.5 | 0.1 |
| Sesame oil | — | — | — | 0.1 | — |
| Polyethylene glycol 400 | 0.1 | — | — | — | — |
| Polyethylene glycol 4000 | — | 1 | 0.1 | 0.5 | 0.1 |
| Pyridoxine hydrochloride | 0.1 | — | — | — | 0.1 |
| Chlorpheniramine maleate | 0.03 | — | — | — | 0.03 |
| Dipotassium glycyrrhizinate | 0.25 | — | — | — | 0.25 |
| Potassium aspartate | — | — | 1 | — | — |

TABLE 9-continued

| | Formulation 17 Eyedrop | Formulation 18 Eyedrop | Formulation 19 Eyedrop | Formulation 20 Eyedrop | Formulation 21 Eyedrop |
|---|---|---|---|---|---|
| Aminoethylsulfonic acid | — | — | — | 1 | — |
| Sodium chondroitin sulfate | 0.5 | 0.5 | 0.5 | 0.5 | 0.5 |
| Hydroxypropylmethyl cellulose 2906 | — | — | 0.1 | — | — |
| Hydroxyethyl cellulose | — | 0.3 | — | 0.3 | — |
| Sodium hyaluronate | — | 0.01 | 0.005 | 0.01 | — |
| Propylene glycol | 0.1 | — | — | — | 0.1 |
| Polysorbate 80 | — | 0.3 | — | 0.7 | — |
| Polyoxyethylene hydrogenated castor oil 60 | 0.1 | — | 0.3 | — | 0.1 |
| Sodium chloride | 0.3 | 0.4 | 0.5 | 0.4 | 0.3 |
| Potassium chloride | 0.05 | 0.1 | 0.1 | 0.1 | 0.05 |
| Calcium chloride | 0.005 | — | 0.005 | — | 0.005 |
| Magnesium chloride | 0.005 | — | 0.002 | — | 0.005 |
| l-menthol | 0.001 | 0.001 | 0.002 | 0.001 | 0.001 |
| d-camphor | — | 0.001 | — | 0.001 | — |
| d-borneol | 0.001 | — | — | — | 0.001 |
| Polyhexanide hydrochloride | 0.0001 | 0.00005 | 0.0001 | — | 0.0001 |
| Chlorohexidine gluconate | — | — | — | 0.005 | — |
| Trometamol | — | — | — | 0.1 | — |
| Sodium edetate | 0.005 | 0.05 | 0.05 | 0.05 | 0.05 |
| Boric acid | 1.5 | 1 | 0.5 | 1 | 1.5 |
| Borax | 0.1 | 0.1 | 0.03 | 0.1 | 0.1 |
| Hydrochloric acid | Proper amount | Proper amount | Proper amount | Proper amount | Proper amount |
| Sodium hydroxide | Proper amount | Proper amount | Proper amount | Proper amount | Proper amount |
| Purified water | Balance | Balance | Balance | Balance | Balance |
| pH | 7 | 6.5 | 7.5 | 7 | 7 |

TABLE 10

| | Formulation 22 Eyedrop | Formulation 23 Eyedrop | Formulation 24 Eyedrop | Formulation 25 Eyedrop |
|---|---|---|---|---|
| Polyvinyl pyrrolidone K90 | 0.5 | 0.5 | 0.05 | 0.1 |
| Sesame oil | — | — | 0.1 | — |
| Polyethylene glycol 6000 | 1 | 0.1 | 0.5 | 0.1 |
| Pyridoxine hydrochloride | — | — | — | 0.1 |
| Chlorpheniramine maleate | — | — | — | 0.03 |
| Dipotassium glycyrrhizinate | — | — | — | 0.25 |
| Potassium aspartate | — | 1 | — | — |
| Aminoethylsulfonic acid | — | — | 1 | — |
| Sodium chondroitin sulfate | 0.5 | 0.5 | 0.5 | 0.5 |
| Hydroxypropylmethyl cellulose 2906 | — | 0.1 | — | — |
| Hydroxyethyl cellulose | 0.3 | — | 0.3 | — |
| Sodium hyaluronate | 0.01 | 0.005 | 0.01 | — |
| Propylene glycol | — | — | — | 0.1 |
| Polysorbate 80 | 0.3 | — | 0.3 | — |
| Polyoxyethylene hydrogenated castor oil 60 | — | 0.3 | 0.3 | 0.1 |
| Sodium chloride | 0.4 | 0.5 | 0.4 | 0.3 |
| Potassium chloride | 0.1 | 0.1 | 0.1 | 0.05 |
| Calcium chloride | — | 0.005 | — | 0.005 |
| Magnesium chloride | — | 0.002 | — | 0.005 |
| l-menthol | 0.001 | 0.002 | 0.001 | 0.001 |
| d-camphor | 0.001 | — | 0.001 | — |
| d-borneol | — | — | — | 0.001 |
| Polyhexanide hydrochloride | 0.00005 | 0.0001 | 0.00015 | — |
| Chlorohexidine gluconate | — | — | — | 0.005 |
| Trometamol | — | — | — | 0.1 |
| Sodium edetate | 0.05 | 0.05 | 0.05 | 0.05 |
| Boric acid | 1 | 0.5 | 1 | 1 |
| Borax | 0.1 | 0.03 | 0.1 | 0.1 |
| Hydrochloric acid | Proper amount | Proper amount | Proper amount | Proper amount |
| Sodium hydroxide | Proper amount | Proper amount | Proper amount | Proper amount |
| Purified water | Balance | Balance | Balance | Balance |
| pH | 6.5 | 7.5 | 7 | 7 |

TABLE 11

|  | Formulation 26 Eyewash solution | Formulation 27 Contact lens sterilization/ Cleaning/storage solution | Formulation 28 Contact lens wetting solution |
|---|---|---|---|
| Polyvinyl pyrrolidone K90 | 0.5 | 0.1 | 1 |
| Sesame oil | 0.01 | — | 0.05 |
| Polyethylene glycol 400 | 1 | 0.5 | 1 |
| Polyethylene glycol 4000 | — | 0.1 | — |
| Polyethylene glycol 6000 | 0.1 | — | 0.1 |
| Pyridoxine hydrochloride | 0.01 | — | — |
| Chlorpheniramine maleate | 0.025 | — | — |
| Dipotassium glycyrrhizinate | 0.025 | — | — |
| Potassium aspartate | 0.05 | — | 1 |
| Aminoethylsulfonic acid | 0.05 | — | — |
| Sodium condroitin sulfate | 0.05 | — | 0.5 |
| Hydroxypropylmethyl cellulose 2906 | — | — | 0.2 |
| Sodium hyaluronate | 0.005 | 0.001 | 0.005 |
| Polysorbate 80 | — | — | 0.3 |
| Polyoxyethylene hydrogenated castor oil 60 | 0.2 | 0.05 | 0.1 |
| Sodium chloride | 0.3 | 0.4 | 0.4 |
| Potassium chloride | 0.1 | 0.1 | 0.1 |
| Calcium chloride | 0.005 | — | — |
| Magnesium chloride | 0.005 | — | — |
| l-menthol | 0.001 | — | — |
| d-camphor | 0.001 | — | — |
| d-borneol | 0.001 | — | — |
| Polyhexanide hydrochloride | 0.00005 | 0.0001 | — |
| Chlorohexidine gluconate | — | — | 0.005 |
| Sodium edetate | 0.05 | 0.05 | 0.05 |
| Boric acid | 1 | 1 | 1 |
| Borax | 0.1 | 0.1 | 0.1 |
| Hydrochloric acid | Proper amount | Proper amount | Proper amount |
| Sodium hydroxide | Proper amount | Proper amount | Proper amount |
| Purified water | Balance | Balance | Balance |
| pH | 7 | 7 | 7.5 |

Formulations 29 to 32 are shown in both Table 12 and Table 13, and Formulations 33 to 36 are shown in both Table 14 and Table 15. In Tables 12 to 15, the proportions of the respective components are expressed in a unit of w/v %. Pharmaceutical products 56 to 63 were respectively produced by filling eyedrops of Formulations 29 to 36 in polyethylene terephthalate containers and attaching polyethylene nozzles to the respective polyethylene terephthalate containers. Pharmaceutical products 64 to 71 were respectively produced by filling the eyedrops of Formulations 29 to 36 in polyethylene terephthalate containers and attaching polybutylene terephthalate nozzles to the respective polyethylene terephthalate containers.

TABLE 12

|  | Formulation 29 Eyedrop | Formulation 30 Eyedrop | Formulation 31 Eyedrop | Formulation 32 Eyedrop |
|---|---|---|---|---|
| Polyvinyl pyrrolidone K90 | 0.01 | 0.05 | 0.005 | 0.05 |
| Sesame oil | 0.05 | 0.02 | 0.05 | 0.1 |
| Castor oil | — | — | — | — |
| Polyethylene glycol 400 | — | — | — | — |
| Polyethylene glycol 4000 | — | — | — | 1 |
| Polyethylene glycol 6000 | — | — | 0.2 | — |
| Neostigmine methylsulfate | — | — | — | — |
| Pyridoxine hydrochloride | — | 0.05 | — | — |
| Panthenol | — | — | — | — |
| Tocopherol acetate | — | — | — | — |
| Retinol Palmitate | — | — | — | — |
| Cyanocobalamin | — | — | — | — |
| Chlorpheniramine maleate | — | — | — | — |
| Allantoin | — | — | — | — |
| Dipotassium glycyrrizinate | — | 0.1 | — | — |
| ε-aminocaproic acid | — | — | — | — |
| Potassium aspartate | — | 1 | — | 0.5 |
| Aminoethylsulfonic acid | — | — | 1 | 0.5 |
| Sodium chondroitin sulfate | — | 0.25 | 0.5 | — |
| Hydroxypropylmethyl cellulose 2906 | — | 0.1 | — | 0.05 |
| Hydroxyethyl cellulose | 0.3 | — | 0.1 | — |
| Sodium hyaluronate | 0.002 | — | 0.1 | 0.002 |
| Propylene glycol | — | — | — | — |
| Polysorbate 80 | 0.3 | — | 0.1 | — |
| Polyoxyethylene hydrogenated castor oil 60 | — | 0.05 | — | 0.3 |
| Polyoxyethylene castor oil 10 | — | — | 0.2 | — |

TABLE 12-continued

|  | Formulation 29 Eyedrop | Formulation 30 Eyedrop | Formulation 31 Eyedrop | Formulation 32 Eyedrop |
|---|---|---|---|---|
| Polyoxyl 40 monostearate | — | — | 0.1 | — |
| Poloxamer 407 | — | 0.1 | — | 0.05 |

TABLE 13

|  | Formulation 29 Eyedrop | Formulation 30 Eyedrop | Formulation 31 Eyedrop | Formulation 32 Eyedrop |
|---|---|---|---|---|
| Sodium chloride | 0.4 | 0.5 | 0.4 | 0.5 |
| Potassium chloride | 0.1 | 0.1 | 0.1 | 0.1 |
| Calcium chloride | — | 0.005 | — | — |
| Magnesium chloride | — | — | — | — |
| d-menthol | 0.005 | 0.002 | 0.001 | — |
| l-camphor | 0.001 | — | 0.001 | — |
| d-borneol | — | 0.001 | 0.002 | — |
| Benzalkonium chloride | — | — | — | 0.01 |
| Polyhexanide hydrochloride | 0.00005 | — | — | — |
| Chlorohexidine gluconate | — | — | — | — |
| Potassium sorbate | — | — | 0.1 | — |
| Trometamol | — | 0.1 | — | — |
| Sodium edetate | 0.01 | 0.05 | — | 0.01 |
| Boric acid | 1 | 0.5 | 1 | 0.5 |
| Borax | 0.1 | 0.03 | 0.1 | 0.03 |
| Sodium hydrogen phosphate | — | — | — | — |
| Sodium dihydrogen phosphate | — | — | — | — |
| Hydrochloric acid | Proper amount | Proper amount | Proper amount | Proper amount |
| Sodium hydroxide | Proper amount | Proper amount | Proper amount | Proper amount |
| Purified water | Balance | Balance | Balance | Balance |
| pH | 7.3 | 7 | 7.5 | 6 |

TABLE 14

|  | Formulation 33 Eyedrop | Formulation 34 Eyedrop | Formulation 35 Eyedrop | Formulation 36 Eyedrop |
|---|---|---|---|---|
| Polyvinyl pyrrolidone K90 | 0.005 | 0.1 | 0.005 | 0.01 |
| Sesame oil | 0.02 | 0.01 | — | 0.05 |
| Castor oil | — | — | 0.05 | — |
| Polyethylene glycol 400 | — | — | 0.1 | — |
| Polyethylene glycol 4000 | — | — | — | — |
| Polyethylene glycol 6000 | — | — | — | — |
| Neostigmine methylsulfate | — | — | — | 0.005 |
| Pyridoxine hydrochloride | 0.1 | — | — | 0.05 |
| Panthenol | — | — | — | 0.1 |
| Tocopherol acetate | — | — | — | 0.025 |
| Retinol Palmitate | — | — | — | 45000 unit |
| Cyanocobalamin | — | — | — | 0.02 |
| Chlorpheniramine maleate | 0.03 | — | 0.015 | 0.015 |
| Allantoin | — | — | — | 0.15 |
| Dipotassium glycyrrhizinate | 0.125 | — | 0.25 | 0.125 |
| ε-aminocaproic acid | — | — | — | 1 |
| Potassium aspartate | — | — | — | 0.5 |
| Aminoethylsulfonic acid | — | — | — | 0.5 |
| Sodium chondroitin sulfate | — | 0.1 | 0.5 | 0.25 |
| Hydroxypropylmethyl cellulose 2906 | — | — | 0.3 | 0.1 |
| Hydroxyethyl cellulose | — | — | — | — |
| Sodium hyaluronate | — | 0.005 | — | — |
| Propylene glycol | 0.5 | — | — | — |
| Polysorbate 80 | — | 0.05 | — | — |
| Polyoxyethylene hydrogenated castor oil 60 | 0.4 | — | 0.1 | 0.2 |
| Polyoxyethylene castor oil 10 | — | — | — | 0.1 |
| Polyoxyl 40 monostearate | — | — | — | 0.05 |
| Poloxamer 407 | — | — | — | 0.1 |

TABLE 15

| | Formulation 33 Eyedrop | Formulation 34 Eyedrop | Formulation 35 Eyedrop | Formulation 36 Eyedrop |
|---|---|---|---|---|
| Sodium chloride | 0.3 | 0.4 | 0.3 | 0.3 |
| Potassium chloride | 0.05 | 0.1 | 0.05 | 0.05 |
| Calcium chloride | — | — | 0.001 | 0.001 |
| Magnesium chloride | — | — | 0.005 | 0.005 |
| d-menthol | 0.001 | 0.01 | 0.005 | 0.001 |
| l-camphor | — | 0.001 | — | — |
| d-borneol | 0.001 | — | — | — |
| Benzalkonium chloride | — | — | — | — |
| Polyhexanide hydrochloride | 0.0001 | — | 0.00005 | 0.0001 |
| Chlorohexidine gluconate | — | 0.005 | — | — |
| Potassium sorbate | — | — | — | — |
| Trometamol | — | — | — | — |
| Sodium edetate | 0.05 | 0.05 | 0.1 | 0.1 |
| Boric acid | — | 1 | 1 | 1 |
| Borax | — | 0.1 | 0.1 | 0.1 |
| Sodium hydrogen phosphate | 0.2 | — | — | — |
| Sodium dihydrogen phosphate | 0.05 | — | — | — |
| Hydrochloric acid | Proper amount | Proper amount | Proper amount | Proper amount |
| Sodium hydroxide | Proper amount | Proper amount | Proper amount | Proper amount |
| Purified water | Balance | Balance | Balance | Balance |
| pH | 7 | 8 | 6.5 | 6 |

While specific forms of the embodiments of the present disclosure have been shown in the aforementioned inventive examples, the inventive examples are merely illustrative of the disclosure but not limitative of the disclosure. It is contemplated that various modifications apparent to those skilled in the art could be made within the scope of the disclosure.

The present disclosure provides an ophthalmic composition which alleviates a sticky sensation after instillation thereof and ensures an excellent use sensation in a wide variety of applications. Further, the present disclosure provides an ophthalmic composition which reduces friction occurring during blinking or during wearing of contact lenses in a wide variety of applications.

The invention claimed is:

1. An ophthalmic composition comprising:
 (A) polyvinyl pyrrolidone K90;
 (B) an oil component comprising at least one selected from the group consisting of sesame oil and castor oil, and
 (C) a nonionic surfactant,
 wherein the polyvinyl pyrrolidone K90 (A) is present in a proportion of 0.001 to 10 w/v % based on a total amount of the ophthalmic composition.

2. The ophthalmic composition according to claim 1, wherein the ophthalmic composition is configured for use in contact lens.

3. The ophthalmic composition according to claim 2, wherein the contact lens is a soft contact lens.

4. The ophthalmic composition according to claim 1, wherein the oil component (B) comprises sesame oil.

5. The ophthalmic composition according to claim 1, wherein the oil component (B) comprises castor oil.

6. The ophthalmic composition according to claim 1, wherein the nonionic surfactant (C) is polyoxyethylene (POE) sorbitan fatty acid esters.

7. A method for imparting an ophthalmic composition with a friction reducing effect, comprising a step of:
 adding polyvinyl pyrrolidone K90 (A), an oil component comprising at least one selected from the group consisting of sesame oil and castor oil (B), and a nonionic surfactant (C) to the ophthalmic composition,
 wherein the polyvinyl pyrrolidone K90 (A) is present in a proportion of 0.001 to 10 w/v % based on a total amount of the ophthalmic composition.

8. The method according to claim 7, wherein the oil component (B) comprises sesame oil.

9. The method according to claim 7, wherein the oil component (B) comprises castor oil.

* * * * *